United States Patent [19]

Ito et al.

[11] Patent Number: 4,623,342
[45] Date of Patent: Nov. 18, 1986

[54] DISPOSABLE DIAPER

[75] Inventors: Osamu Ito, Utsunomiya; Hiroshi Mizutani, Yashiyo; Kazunori Nishizawa, Funabashi, all of Japan

[73] Assignee: Kao Corporation, Tokyo, Japan

[21] Appl. No.: 668,234

[22] Filed: Nov. 5, 1984

[30] Foreign Application Priority Data

Nov. 7, 1983 [JP] Japan ............................. 58-208705

[51] Int. Cl.$^4$ ............................................. A61F 13/16
[52] U.S. Cl. ................................. 604/385 A; 604/378
[58] Field of Search ................ 604/385.1 R, 385.2 A, 604/358, 378, 370, 371, 365, 379

[56] References Cited

U.S. PATENT DOCUMENTS

| 4,246,900 | 1/1981 | Schroder | 604/378 |
| 4,336,803 | 6/1982 | Repke | 604/385 A |
| 4,447,240 | 5/1984 | Ito et al. | 604/385 A |

Primary Examiner—John D. Yasko
Attorney, Agent, or Firm—Flynn, Thiel, Boutell & Tanis

[57] ABSTRACT

A disposable diaper comprises a liquid-permeable surface sheet, a liquid-impermeable backing sheet, and an absorbent pad sandwiched between the two sheets, characterized in that water-absorptive, shrinkable fiber strings, which contract lengthwise on contact with water and are rendered stretchable, are secured to the two sheets, extending midway longitudinally of the diaper in parallel along, but without overlapping, the both edges of the pad, the edge portions of the surface sheet outside the water-absorptive, shrinkable fiber strings and the surface sheet portion on the absorbent pad being partly bonded together at two spots about halfway of the length, the distance between the two bonded spots being at least 50 mm and the bonded spots themselves being 10 to 50 mm long each, and elastic, stretch members, at least 70 mm long each and having a combined elastic force or tensile strength (the weight equivalent to the force required to stretch the diaper including any shrank portions thereof up to the total diaper length) of 20 to 600 g, are provided midway and longitudinally of the both edge portions of the diaper at least 5 mm outside the both bonded spots.

9 Claims, 4 Drawing Figures

DISPOSABLE DIAPER

This invention relates to a disposable diaper having a leakproof seal means.

Various leakproof designs for disposable diapers have hitherto been proposed. A typical group of them, as disclosed in Japanese Patent Publication No. 40267/1977 and Japanese Patent Laid-Open Nos. 115939/1979 and 120045/1977, form gathers along the both edges of a disposable diaper by elastic members fitted to the edges longitudinally of the diaper so as to keep the diaper in intimate contact with the thighs of the wearer and minimize the leakage of excretions. Another seal design taught in Japanese Patent Laid-Open No. 35002/1982, uses water-absorptive, shrinkable fiber strings which contract on wetting along the edges longitudinally of a disposable diaper so as to fit the diaper tightly to the wearer and minimize the leakage.

These leakproof designs of the prior art have disadvantages, however. The seal means of the former group, which utilize the elastic shrinking forces of elastic material such as rubber, have to be pressed against the thighs of the wearer tightly enough to avoid urine leakage. Fastening which is too light often results in reddish inflammation, irritation, or injury of the thighs. In addition, the close contact of the diaper tends to make the skin hot and moist.

The latter design also has the disadvantage of inviting frequent leakage of feces when the wearer evacuates the bowels, discharging especially watery or loose feces, before urination. This is because the water-absorptive, shrinkable fiber strings cannot gather the edges of the diaper unless they are wet with urine.

With the view to overcoming these disadvantages of the two prior art concepts, the present inventors have made intense studies and have now arrived at this invention.

The present invention provides a disposable diaper comprising a liquid-permeable surface sheet, a liquid-impermeable backing sheet, and an absorbent pad sandwiched between the two sheets, characterized in that water-absorptive, shrinkable fiber strings, which contract lengthwise on contact with water and are rendered stretchable, are secured to the two sheets, extending midway longitudinally of the diaper in parallel along, but without overlapping, the both edges of the pad, the edge portions of the surface sheet outside the water-absorptive, shrinkable fiber strings and the surface sheet portion on the absorbent pad being partly bonded together at two spots about halfway of the length, the distance between the two bonded spots being at least 50 mm and the bonded spots themselves being 10 to 50 mm long each, and elastic, stretch members, at least 70 mm long each and having a combined elastic force or tensile strength (the weight equivalent to the force required to stretch the diaper including any shrunken portions thereof up to the total diaper length) of 20 to 600 g, are provided midway and longitudinally of the both edge portions of the diaper at least 5 mm outside the both bonded spots.

Figure 1:
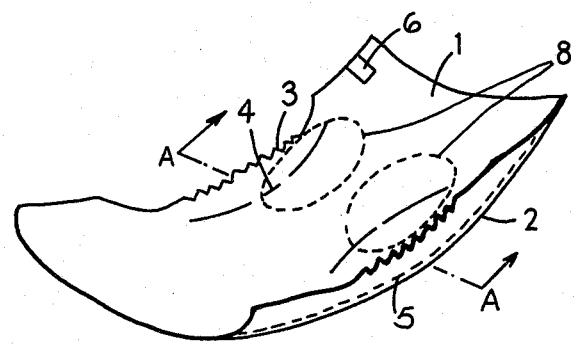
FIG. 1 is a perspective view of an embodiment of the disposable diaper of the invention.
Figure 2:
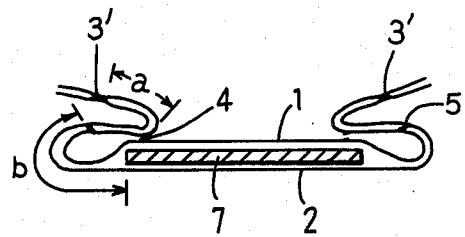
FIG. 2 is a sectional view taken along the line A—A of FIG. 1.
Figure 3:
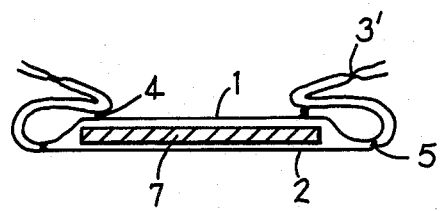
FIGS. 3 and 4 are sectional views of other embodiments, respectively.

The invention will now be described in more detail in connection with embodiments thereof shown in the accompanying drawings.

The disposable diaper embodying the invention comprises a liquid-permeable surface sheet 1, a liquid-impermeable backing sheet 2, and an absorbent pad 7, with two strings 5 of a fiber, which contracts lengthwise on contact with water and is rendered stretchable, secured to the two sheets in parallel along, but without overlapping, the both edges of the absorbent pad 7. The edge portions of the surface sheet 1 outside the water-absorptive, shrinkable fiber strings 5 and portions of the surface sheet that overlie the absorbent pad 7 are partly bonded together at two spots halfway of the length. These bonded areas 4 are referred to herein as leg spots. Between the superposed sheet portions farther outside the leg spots, there are secured two elastic, stretch members 3' designed to provide elastic gathers 3 outside these spots.

This disposable diaper is aimed at absorbing the urine and feces of the wearer without any leakage outside or excessive pressure upon the skin. The functions of the diaper will now be explained. The leg spots 4 combine with the elastic gathers 3 to form pockets 8 in the diaper between the buttocks and thighs of the wearer. The pockets prevent leakage of feces out of the diaper while the latter is not wet with urine. In case of urination, the water-absorptive, shrinkable fiber strings 5 prevent the leakage out of the diaper edges facing the thighs of the wearer. The elastic gathers 3 have to be just tight enough to form the pockets. Since the diaper uses no highly elastic stretch member, the pressure to be exerted upon the skin of the wearer is negligible, and leakage of urine and feces out of the diaper is avoided.

It is important here to form effective pockets by means of the gathers 3 and the leg spots 4. In attaining this end the location and length of the elastic, stretch members and the length of the leg spots are critical. In order to provide the useful pockets it is necessary that the two leg spots be spaced apart a distance of at least 50 mm and the leg spots be 10 to 50 mm long each. Also, the distance (a) between each leg spot 4 and the associated elastic, stretch member 3' must be at least 5 mm. If the distance is less than 5 mm, the resistance of the leg spot will render it difficult to form effective gathers in that area. Moreover, the resulting pocket will be so shallow and small that frequent leakage will result.

As regards the length of the elastic, stretch members, too short members will fail to form pockets which effectively prevent leakage of feces. The members should, therefore, have a length in a stretched state of at least 70 mm, preferably not shorter than 100 mm.

Another important factor is the elasticity of the elastic, stretch members. Closely related to the pressure upon the skin, the elasticity should be the lowest possible for the diapered person. Thus, it should be at a minimum required for forming effective gathers. In this respect the diaper of the invention, which utilizes water-absorptive, shrinkable fiber strings, need no elastic gathers for preventing urine leakage but gathers just enough for forming pockets. Only slightly elastic, stretch members are needed. In connection with the pressure upon the skin, a diaper having a tensile strength of more than 600 g when stretched will make the wearer uncomfortable. On the other hand, a strength of at least 20 g is required for the purpose of gathering. Any material which has such a tensile strength may be used for the elastic, stretch member.

It is preferable that the strength of the elastic, stretch member be in the range of 20 to 100 g. In this preferable embodiment, it may be made of ordinary natural rubber, urethane rubber, or any other elastic material. Among the useful members, the most desirable is one formed of fine urethane filaments matted into nonwoven cloth and elasticized by the spun bond method. Such a member is the best as it is soft to the touch and yet forms effective gathers.

Another preferable range of the tensile strenth of the elastic, stretch member is from 50 to 600 g when stretched. More preferably, it is from 20 to 150 g when it is elongated by 20 percent. A material suitable for this preferable embodiment is polyurethane, polybutadiene, a copolymer of ethylene and vinyl acetate, modified polyethylene and a composition containing any of the beforegoing, for example in the form of a sheet or foamed sheet.

The elastic, stretch member is preferred to have a width of 4 mm or larger, especially 5 mm or larger. For example the width of 4 to 40 mm is practicable to lessen the pressure on the skin of the user.

If the water-absorptive, shrinkable fiber strings are located close to the absorbent pad, they can be kept from shrinking by the pad. In order to attain more effective shrinkage, the strings must be kept at a certain distance away from the pad. For the intimate contact of the diaper with the skin of the wearer by dint of the shrinkage of the water-absorptive, shrinkable fiber strings, the distance (b) between each edge of the absorbent pad and the associated string should be at least 10 mm. This spaced relation is helpful in avoiding the leakage of urine out of the diaper edge.

The water-absorptive, shrinkable fiber strings so far described are effective if they are made up of twisted yarns of a carboxymethylcellulose, hydrolyzed acrylic fiber or the like as disclosed in Japanese Patent Laid-Open No. 35002/1982. Desirably, the water-absorptive, shrinkable fiber strings are provided with means for conducting urine out of the absorbent pad into the strings.

While preferred embodiments of the disposable diaper of the invention have been described, it is to be understood that the invention is not limited thereto but various modifications may be made within the scope of the invention.

EXAMPLES 1 TO 4 AND COMPARATIVE EXAMPLE 1

Figure 4:
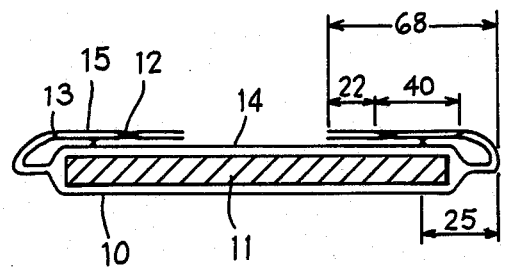

As shown in FIG. 4, a diaper was made by placing an absorbent layer 11 having 150 mm width and 380 mm length at the center of a polyethylene sheet 10 having 300 mm width and 430 mm length; placing an elastic, stretch member 12 each 22 mm inside of the edge of the polyethylene sheet; placing a water-absorptive, shrinkable fiber string 13 each 40 mm inside of the member; covering the resulting assembly with a non-woven sheet 14 having the same size as the polyethylene sheet, folding both non-woven sheet and polyethylene sheet each at 68 mm inside of either edge thereof and making the adhesion between each other at two positions each at 25 mm inside of the folding position. The elastic, stretch member is listed in Table 1 by material. Each has an elastic length of 100 mm.

TABLE 1

| material No. | material | width of the member | when stretched at the maximum | | when stretched at 20% |
|---|---|---|---|---|---|
| | | | elongation percent | elastic force | elastic force |
| 1 | polyethylene composite film | 15 mm | 44% | 310 g | 90 g |
| 2 | polyethylene composite film | 15 mm | 45% | 440 g | 180 g |
| 3 | polyethylene composite film | 10 mm | 42% | 130 g | 45 g |
| 4 | the same as 3 | 5 mm | 35% | 65 g | 25 g |
| 5 | modified polyethylene film | 20 mm | 62% | 640 g | 120 g |

The materials 1 to 3 are each available from Right Co with grade number of 15040, 82035 and 15030, respectively. The material 5 is Tafmer P, a tradename of Mitsui Petroleum Chemical Co., Ltd.

Each obtained diaper was put on babies of various sizes 10 babies of the body weight of 5 to 7 kg, 10 babies of 7 to 9 kg and 10 babies of 9 to 10 kg. The skin where the diaper was attached to the babies was observed after 3 hours had passed. Results are shown in Table 2 giving the number of babies who had red marks in red of the diaper.

TABLE 2

| | material No. | influence on the skin | | |
|---|---|---|---|---|
| | | the babies of 5–7 kg | that of 7–9 kg | that of 9–10 kg |
| Example 1 | 1 | 0 | 0 | 0 |
| Example 2 | 2 | 1 | 0 | 1 |
| Example 3 | 3 | 0 | 0 | 0 |
| Example 4 | 4 | 0 | 0 | 0 |
| Comparative Example 1 | 5 | 0 | 2 | 5 |

The embodiments of the invention in which an exclusive or privilege is claimed are defined as follows:

1. A disposable diaper comprising a liquid-permeable surface sheet, a liquid-impermeable backing sheet, an absorbent pad sandwiched between said two sheets, water-absorptive, shrinkable fiber strings, contractable lengthwise and rendered stretchable on contact with water are secured to said two sheets, said fiber strings being disposed longitudinally to the diaper in parallel along, and in non-overlapping relation to the longitudinal edges of said pad, the longitudinal edge portions of the surface sheet outside the water-absorptive, shrinkable fiber strings and a portion of said surface sheet overlying the absorbent pad being partly bonded together at two spots at about the midpoint of the length of both longitudinal sides of said diaper, the distance between said two bonded spots being at least 50 mm and said bonded spots themselves each being 10 to 50 mm long, and elastic stretch members, each being at least 70 mm long and having a combined elastic force of 20 to 600 g, are disposed longitudinally on both longitudinal edges of the diaper, spaced apart at least 5 mm from said bonded spots.

2. A disposable diaper as defined in claim 1, in which the water-absorptive, shrinkable fiber strings are secured at a distance of at least 10 mm each from the opposite edges of the absorbent pad.

3. A disposable diaper as claimed in claim 1, in which said combined elastic force or tensile strength is in the range of 20 to 100 g.

4. A disposable diaper as claimed in claim 2, in which said combined elastic force or tensile strength is in the range of 20 to 100 g.

5. A disposable diaper as claimed in claim 1, in which said combined elastic force or tensile strength is in the range of 50 to 600 g.

6. A disposable diaper as claimed in claim 2, in which said combined elastic force or tensile strength is in the range of 50 to 600 g.

7. A disposable diaper comprising a liquid-permeable surface sheet, a liquid-impermeable backing sheet, and an elongate absorbent pad disposed between said two sheets, said disposable diaper further comprising water-absorptive, shrinkable fiber strings which contract lengthwise and are rendered stretchable on contact with water, said shrinkable fiber strings being disposed along and spaced from both longitudinal edges of said elongate absorbent pad and being secured to said sheets and spaced apart a first predetermined distance inward from the longitudinal edges of said diaper; and elongate elastic stretch members disposed along and a distance apart from the longitudinal edges of said elongate absorbent pad, said elongate elastic stretch members being spaced apart a second predetermined distance inward from the longitudinal edges of said diaper and forming an elastic leg gather, wherein a first portion of said liquid-permeable surface sheet disposed a thid predetermined distance inward from the longitudinal edges of said diaper is bonded to a second portion of said water-permeable sheet disposed over said absorbent pad to form a pocket thereby, said second predetermined distance being shorter than said third predetermined distance, said third predetermined distance being shorter than said first predetermined distance.

8. A disposable diaper as claimed in claim 7, wherein said liquid-permeable surface sheet is bonded to itself at two points on each longitudinal edge of said diaper, said points of bonding being 10 to 50 mm long each and on each longitudinal side said points being at least 50 mm apart, and said elastic stretch members being at least 70 mm long and having a combined elastic force of from 20 to 600 g and being disposed at least 5 mm spaced apart from said bonded spots.

9. A disposable diaper comprising:

a liquid-permeable surface sheet;

a liquid-impermeable backing sheet;

an absorbent pad between said surface and backing sheets, said absorbent pad being of lesser width than said surface and backing sheets so that said sheets have marginal edge portions that extend beyond the edges of said pads and are in direct face-to-face opposed relation, said marginal edge portions each having first and second, oppositely reversely bent zones in the regions of the diaper that encircle the legs of the wearer wherein, in said first zone, each said marginal edge portion is reversely bent to extend inwardly above said surface sheet to a location above said pad and, in said second zone, each said marginal edge portion is reversely bent to extend outwardly away from said pad;

said marginal edge portions each having an elongated water-absorptive shrinkable fiber string positioned between said sheets at a location between the edge of said pad and said second reversely bent zone, said string extending lengthwise of the diaper and being secured to said surface and backing sheets, said shrinkable fiber string being capable of contracting lengthwise on contact with water and thereby being rendered stretchable;

each of said second reversely bent zones being bonded to the adjacent portion of said surface sheet that overlies said pad and each of said marginal edge portions having an elastic stretch member secured to said surface and backing sheets at a location outwardly from said second reversely bent zone to provide elastic gathers at locations outwardly of said second reversely bent zones whereby to form pockets in the diaper.

* * * * *